United States Patent [19]

Mrozik

[11] Patent Number: 4,530,921
[45] Date of Patent: Jul. 23, 1985

[54] AVERMECTIN EPOXIDE DERIVATIVES AND METHOD OF USE

[75] Inventor: Helmut H. Mrozik, Matawan, N.J.

[73] Assignee: Merck & Co., Inc., Rahway, N.J.

[21] Appl. No.: 538,612

[22] Filed: Oct. 3, 1983

[51] Int. Cl.$^3$ .................. A61K 31/35; A61K 31/71; C07H 17/08

[52] U.S. Cl. .................. 514/30; 514/450; 536/7.1; 549/264; 549/265

[58] Field of Search .......... 536/7.1; 549/265, 264; 424/180, 279; 514/30, 450

[56] References Cited

U.S. PATENT DOCUMENTS

| | | | |
|---|---|---|---|
| 4,056,616 | 11/1977 | Reimann et al. | 536/7.1 |
| 4,199,569 | 4/1980 | Chabala et al. | 536/7.1 |
| 4,206,205 | 6/1980 | Mrozik et al. | 536/7.1 |
| 4,310,519 | 1/1982 | Albers-Schonberg et al. | 536/7.1 |
| 4,454,314 | 6/1984 | Nagel | 536/7.1 |

OTHER PUBLICATIONS

Derwent Abstract 84544E/40, Feb. 23, 1981.
Derwent Abstract 84545E/40, Feb. 23, 1981.

*Primary Examiner*—Johnnie R. Brown
*Attorney, Agent, or Firm*—David L. Rose; Mario A. Monaco

[57] ABSTRACT

There are disclosed novel avermectin compounds wherein certain double bonds are oxidized to epoxides. The epoxides are prepared by oxidizing an avermectin compound with a mild oxidizing agent. The avermectin epoxide compounds have utility as anti-parasitic agents and compositions for that use are also disclosed. The compounds are also highly potent insecticides against agricultural pests.

16 Claims, No Drawings

AVERMECTIN EPOXIDE DERIVATIVES AND METHOD OF USE

BACKGROUND OF THE INVENTION

The term avermectin (previously referred to as C-076) is used to describe a series of compounds isolated from the fermentation broth of an avermectin producing strain of *Streptomyces avermitilis* and derivatives thereof. The morphological characteristics of the culture are completely described in U.S. Pat. No. 4,310,519. The avermectin compounds are a series of macrolides, each of which is substituted thereon at the 13-position with a 4'-(α-L-oleandrosyl)-α-L-oleandrose group. The avermectin compounds and the instant derivatives thereof have a very high degree of anthelmintic and anti-parasitic activity.

Also included are certain synthetically modified avermectins such as 22,23-dihydro avermectin B1a/B1b also known as ivermectin.

The avermectin series of compounds isolated from the fermentation broth have the following structure:

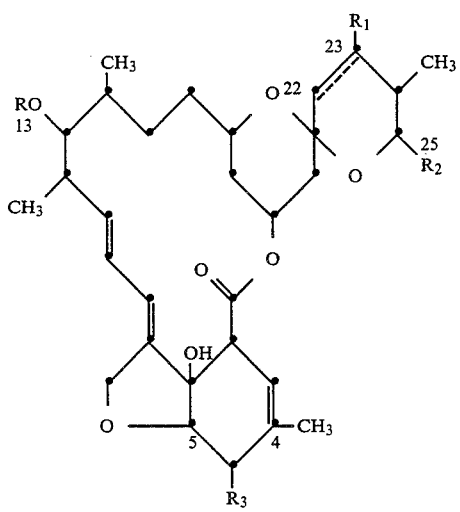

wherein R is the 4'-(α-1-oleandrosyl)-α-1-oleandrose group of the structure:

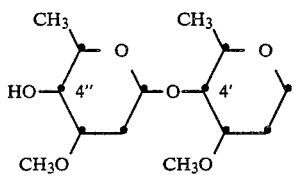

and wherein the broken line indicates a single or a double bond;

R₁ is hydroxy and is present only when said broken line indicates a single bond;
R₂ is iso-propyl or sec-butyl; and
R₃ is methoxy or hydroxy.

There are eight different major avermectin natural product compounds and they are given the designations A1a, A1b, A2a, A2b, B1a, B1b, and B2a based upon the structure of the individual compounds.

In the foregoing structural formula, the individual avermectin compounds are as set forth below. (The R group is 4'(α-L-oleandrosyl)-α-L-oleandrose):

|     | $R_1$       | $R_2$      | $R_3$   |
|-----|-------------|------------|---------|
| A1a | Double Bond | sec-butyl  | —OCH₃   |
| A1b | Double Bond | iso-propyl | —OCH₃   |
| A2a | —OH         | sec-butyl  | —OCH₃   |
| A2B | —OH         | iso-propyl | —OCH₃   |
| B1a | Double Bond | sec-butyl  | —OH     |
| B1b | Double Bond | iso-propyl | —OH     |
| B2a | —OH         | sec-butyl  | —OH     |
| B2b | —OH         | iso-propyl | —OH     |

The avermectin compounds are generally isolated as mixtures of a and b components. Such compounds differ only in the nature of the $R_2$ substituent and the minor structural differences have been found to have very little effect on the isolation procedures, chemical reactivity and biological activity of such compounds.

SUMMARY OF THE INVENTION

The instant invention is concerned with certain derivatives of avermectin compounds wherein the 8,9 and/or 14,15 double bonds are oxidized to epoxides. Thus it is an object of the instant invention to describe such avermectin epoxide compounds. A further object is to describe processes for the preparation of such compounds. A still further object is to describe the uses of such compounds as anti-parasitic agents. Still further objects will become apparent from a reading of the following description.

DESCRIPTION OF THE INVENTION

The compounds of the instant invention have the following structural formula.

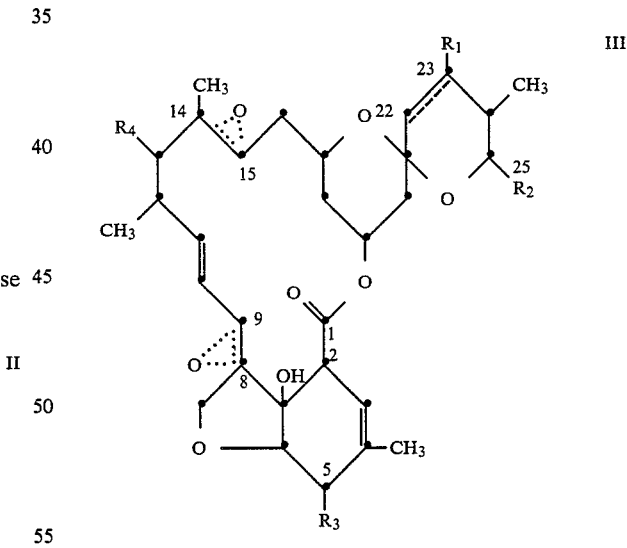

wherein the broken line at the 22,23-position indicates a single or double bond;

R₁ is hydrogen or hydroxy provided that R₁ is present only when the broken line at the 22,23-position indicates a single bond;
R₂ is iso-propyl or sec-butyl;
R₃ is hydroxy or methoxy;
R₄ hydroxy, α-L-oleandrosyloxy, or α-L-oleandrosyl-α-L-oleandrosyloxy, and the triangular figures at 8,9 and 14,15 indicate that there is present either a double bond or an epoxide, provided that at least one of the 8,9 and 14,15 prositions is an epoxide.

Examples of preferred compounds of this invention are as follows:
Avermectin B1a/B1b-8,9-oxide;
Avermectin B1a/B1b-14,15-oxide;
Avermectin B1a/B1b-8,9,14,15-dioxide;
22,23-Dihydro avermectin B1a/B1b-8,9-oxide;
22,23-Dihydro avermectin B1a/B1b-14,15-oxide;
Avermectin B1a/B1b monosaccharide-8,9-oxide;
22,23-Dihydro avermectin B1a/B1b monosaccharide-8,9-oxide;
Avermectin A2a/A2b-8,9-oxide;
Avermectin B2a/B2b-8,9-oxide.

The "b" compounds, those with a 25-isopropyl group, are very difficult to separate from the corresponding "a" compound with a 25-sec-butyl group and as such the compounds are generally isolated as mixtures of the two compounds. Thus references in the instant application to "a" compounds such as B1a, A1a, and the like, are construed to define the pure compound as well as those which actually contain a certain proportion of the corresponding "b" compound. Alternatively, this representation of a mixture is sometimes done by referring to the B1 or B2 compounds or by separating the "a" compound from the "b" compound by a slash (/) such as B1a/B1b, B2a/B2b and the like.

The epoxide compounds of this invention are prepared by treating the appropriately substituted avermectin compound with a mild oxidizing agent. The oxidizing agent should be capable of preparing the epoxide from the 8,9 and 14,15 double bonds, but not be so strong as to completely cleave the bond or to effect any of the other unsaturations or other functional groups present on the molecule. It has been found that oxidizing agents with such characteristics are exemplifid by m-chloroperbenzoic acid, alkyl hydroperoxides catalyzed with vanadyl acetylacetonates, and the like.

The reaction is carried out in an inert solvent, not capable of being oxidized, such as methylene chloride, chloroform, and the like. In order to prevent the reaction from becoming too vigorous, it is carried out at moderate temperatures. Generally, room temperature is adequate although cooling to a temperature of about 0° C. is acceptable. The reaction is usually complete in a fairly short time, up to about 2 hours, at room temperature. The compounds of this invention are isolated using techniques known to those skilled in the art.

Generally, a slight excess of the oxidizing agent is employed such as from about 10 to 30% excess, when it is desired to prepare the 8,9-epoxide. When the 14,15 or both epoxides are desired, an amount of oxidizing agent equivalent to a slight excess of two moles is employed. Such conditions produce a mixture of all these epoxides which are readily separated using chromatographic techniques.

PREPARATION OF STARTING MATERIALS

The ultimate starting materials for the compounds of this invention are the avermectin fermentation products defined above. Thus it is apparent that additional reactions are required to prepare many of the starting materials for the instant compounds. Specifically, reactions are carried out at the 4, 22, and 23-positions. It is generally preferred to prepare whatever substituents are required at these positions before carrying out the reaction to introduce the epoxide on the substrate. Such a procedure generally avoids undesirable side reactions. This technique is not required, however, and if desired other sequences may be used. In addition, during the oxidation reaction described above, it is generally advisable to protect the 5-hydroxy group to prevent the activation and possible oxidation of the 3,4-double bond. With the appropriate positions protected, the oxidation reaction may be carried out without affecting the remainder of the molecule. Subsequent to any of the above described reactions the protecting group may be removed and the unprotected product isolated. The protecting group employed is ideally one which may be readily synthesized, will not be affected by the reaction with the oxidation reagent and may be readily removed without affecting any other functions of the molecule. It is noted that the instant protected compounds are novel and have considerable antiparasitic activity. They are included within the ambit of the instant invention. One preferred type of protecting group for the avermectin and milbemycin type of molecule is the tri-substituted silyl group, preferably the trialkyl silyl group. One especially preferred example, is the t-butyl dimethylsilyl group. The reaction preparing the protected compound is carried out by reacting the hydroxy, usually the 5-hydroxy, compound with the appropriately substituted silylhalide, preferably the silylchloride in an aprotic polar solvent such as dimethylformamide. Imidazole is added as a catalyst. The reaction is complete in from 1 to 24 hours at from 0 to 25° C. For the 5-position hydroxy group the reaction is complete in from ½ to 3 hours at from 0° C. to room temperature. This reaction is selective to the 5 position under the conditions above described and very little, if any, silylation is observed at other hydroxy substituted positions.

The silyl group have been removed after the other contemplated reactions have been carried out. The silyl group or groups are removed by stirring the silyl compound in methanol catalized by a catalytic amount of an acid, preferably a sulfonic acid such as p-toluene sulfonic acid. The reaction is complete in about 1 to 12 hours at from 0° to 50° C.

Another of the starting materials used in the foregoing reaction scheme are those in which the 22,23 double bond of the A1 and B1 compounds has been reduced to a single bond. As is readily apparent from an analysis of the structure of avermectin starting materials there are 5 unsaturations in the "1"-series of compounds. Thus in the "1"series of compounds it is possible to selectively reduce the 22,23 double bond while not affecting the remaining four unsaturations or any other functional group present on the molecule. It is necessary to select a specific catalyst for the hydrogenation, one that will selectively hydrogenate the least hindered from among a series of unsaturations. The preferred catalyst for such a selective hydrogenation procedure is one having the formula:

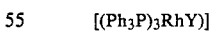

$$[(Ph_3P)_3RhY)]$$

wherein
Ph is phenyl and Y is halogen. The reduction procedure is completely described in U.S. Pat. No. 4,199,569 to Chabala et al.

Additional reactions which may be carried out to prepare the compounds of this invention are the selective removal of one of the α-L-oleandrosyl moieties (described in U.S. Pat. No. 4,206,205 to Mrozik et al.).

The reaction conditions which are generally applicable to the preparation of both the monosaccharide and aglycone involve dissolving the avermectin compound or the hydrogenated avermectin compound in an aqueous acidic non-nucleophilic organic solvent, miscible with water, preferably dioxane, tetrahydrofuran, dimethoxyethane, dimethylformamide, bis-2-methoxyethyl ether, and the like, in which the water concentration is from 0.1 to -20% by volume. Concentrated acid is added to the aqueous organic solvent to the extent of 0.01 to 10% by volume. The reaction mixture is generally stirred at about 20°-40° C., preferably at room temperature, for from 6 to 24 hours. The lower concentration of acid, from about 0.01 to 0.1% will predominately produce the monosaccharide under the above reaction conditions. Higher acid concentrations, from about 1 to 10% will predominantly produce the aglycone under the above reaction conditions. Intermediate acid concentrations will generally produce mixtures of monosaccharide and aglycone. The products are isolated, and mixtures are separated by techniques such as column, thin layer preparative and high pressure liquid chromatography, and other known techniques.

The acids which may be employed in the above process include mineral acids and organic acids such as sulfuric, hydrohalic, phosphoric, trifluoroacetic, trifluoro methane sulfonic and the like. The hydrohalic acids are preferably hydrochloric or hydrobromic. The preferred acid in the above process is sulfuric acid.

A further procedure for the preparation of the monosaccharide or aglycone of the avermectin compounds or of the hydrogenated avermectin compounds utilizes a different solvent system for the monosaccharide and the aglycone. The procedure for the preparation of the monosaccharide uses 1% acid by volume in isopropanol at from 20°-40° C., preferably room temperature, for from 6 to 24 hours. For the preparation of the aglycone, 1% acid, by volume, in methanol under the foregoing reaction conditions has been found to be appropriate.

When this procedure is employed on the starting materials containing the 22,23-double bond, there is a possibility of an acid catalyzed addition of the solvent to the double bond. If such occurs, chromatographic purification will remove the by-product in order to allow for further reactions.

The acids listed above are appropriate for this process, and again sulfuric acid is the preferred acid.

The novel compounds of this invention have significant parasiticidal activity as anthelmintics, ectoparasiticides, insecticides and acaricides, in human and animal health and in agriculture.

The disease or group of diseases described generally as helminthiasis is due to infection of an animal host with parasitic worms known as helminths. Helminthiasis is a prevalent and serious economic problem in domesticated animals such as swine, sheep, horses, cattle, goats, dogs, cats and poultry. Among the helminths, the group of worms described as nematodes causes widespread and often times serious infection in various species of animals. The most common genera of nematodes infecting the animals referred to above are Haemonchus, Trichostrongylus, Ostertagia, Nematodirus, Cooperia, Ascaris, Bunostomum, Oesophagostomum, Chabertia, Trichuris, Strongylus, Trichonema, Dictyocaulus, Capillaria, Heterakis, Toxocara, Ascaridia, Oxyuris, Ancylostoma, Uncinaria, Toxascaris and Parascaris. Certain of these, such as Nematodirus, Cooperia and Oesphagostomum attack primarily the intestinal tract while others, such as Haemonchus and Ostertagia, are more prevalent in the stomach while still others such as Dictyocaulus are found in the lungs. Still other parasites may be located in other tissues and organs of the body such as the heart and blood vessels, subcutaneous and lymphatic tissue and the like. The parasitic infections known as helminthiases lead to anemia, malnutrition, weakness, weight loss, severe damage to the walls of the intestinal tract and other tissues and organs and, if left untreated, may result in death of the infected host. The substituted avermectin compounds of this invention have unexpectedly high activity against these parasites, and in addition are also active against Dirofilaria in dogs, Namatospiroides, Syphacia, Aspiculuris in rodents, arthropod ectoparasites of animals and birds such as ticks, mites, lice, fleas, blowfly, in sheep Lucilia sp., biting insects and such migrating diperous larvae as Hypoderma sp. cattle, Gastrophilus in horses, and Cuterebra sp. in rodents.

The instant compounds are also useful against parasites which infect humans. The most common genera of parasites of the gastro-intestinal tract of man are Ancylostoma, Necator, Ascaris, Strongyloides, Trichinella, Capillaria, Trichuris, and Enterobius. Other medically important genera of parasites which are found in the blood or other tissues and organs outside the gastrointestinal tract are the filiarial worms such as Wuchereria, Brugia, Onchocerca and Loa, Dracunculus and extra intestinal stages of the intestinal worms Strongyloides and Trichinella. The compounds are also of value against arthropods parasitizing man, biting insects and other dipterous pests causing annoyance to man.

The compounds are also active against household pests such as the cockroach, Blatella sp., clothes moth, Tineola sp., carpet beetle, Attagenus sp., and the housefly Musca domestica.

The compounds are also useful against insect pests of stored grains such as Tribolium sp., Tenebrio sp. and of agricultural plants such as spider mites, (Tetranychus sp.), aphids, (Acyrthiosiphon sp.); against migratory orthopterans such as locusts and immature stages of insects living on plant tissue. The compounds are useful as a nematocide for the control of soil nematodes and plant parasites such as Meloidogyne spp. which may be of importance in agriculture The compounds are active against other plant pests such as the southern army worm and Mexican bean beetle larvae.

These compounds may be administered orally in a unit dosage form such as a capsule, bolus or tablet, or as a liquid drench where used as an anthelmintic in mammals. The drench is normally a solution, suspension or dispersion of the active ingredient usually in water together with a suspending agent such as bentonite and a wetting agent or like excipient. Generally, the drenches also contain an antifoaming agent. Drench formulations generally contains from about 0.001 to 0.5% by weight of the active compound. Preferred drench formulations may contain from 0.01 to 0.1% by weight. The capsules and boluses comprise the active ingredient admixed with a carrier vehicle such as starch, talc, magnesium stearate, or di-calcium phosphate.

Where it is desired to administer the avermectin derivatives in a dry, solid unit dosage form, capsules, boluses or tablets containing the desired amount of active compound usually are employed. These dosage forms are prepared by intimately and uniformly mixing the active ingredient with suitable finely divided diluents, fillers, disintegrating agents and/or binders such as starch, lactose, talc, magnesium stearate, vegetable gums and the like. Such unit dosage formulations may be varied widely with respect to their total weight and content of the antiparasitic agent depending upon factors such as the type of host animal to be treated, the severity and type of infection and the weight of the host.

When the active compound is to be administered via an animal feedstuff, it is intimately dispersed in the feed or used as a top dressing or in the form of pellets which may then be added to the finished feed or optionally fed separately. Alternatively, the antiparasitic compounds of our invention may be administered to animals parenterally, for example, by intraruminal, intramuscular, intratracheal, or subcutaneous injection in which event the active ingredient is dissolved or dispersed in a liquid carrier vehicle. For parenteral administration, the active material is suitably admixed with an acceptable vehicle, preferably of the vegetable oil variety such as peanut oil, cotton seed oil and the like. Other parenteral vehicles such as organic preparation using solketal, glycerol formal, and aqueous parenteral formulations are also used. The active avermectin compound or compounds are dissolved or suspended in the parenteral formulation for administration; such formulations generally contain from 0.005 to 5% by weight of the active compound.

Although the antiparasitic agents of this invention find their primary use in the treatment and/or prevention of helminthiasis, they are also useful in the prevention and treatment of diseases caused by other parasites, for example, arthropod parasites such as ticks, lice, fleas, mites and other biting insects in domesticated animals, and poultry. They are also effective in treatment of parasitic diseases that occur in other animals including humans. The optimum amount to be employed for best results will, of course, depend upon the particular compound employed, the species of animal to be treated and the type and severity of parasitic infection or infestation. Generally good results are obtained with our novel compounds by the oral administration of from about 0.001 to 10 mg per kg of animal body weight, such total dose being given at one time or in divided doses over a relatively short period of time such as 1-5 days. With the preferred compounds of the invention, excellent control of such parasties is obtained in animals by administering from about 0.025 to 0.5 mg per kg of body weight in a single dose. Repeat treatments are given are given as required to combat reinfections and are dependent upon the species of parasite and the husbandry techniques being employed. The techniques for administering these materials to animals are known to those skilled in the veterinary field.

When the compounds described herein are administered as a component of the feed of the animals, or dissolved or suspended in the drinking water, compositions are provided in which the active compound or compounds are intimately dispersed in an inert carrier or diluent. By inert carrier is meant one that will not react with the antiparasitic agent and one that may be administered safely to animals. Preferably, a carrier for feed administration is one that is, or may be, an ingredient of the animal ration.

Suitable compositions include feed premixes or supplements in which the active ingredient is present in relatively large amounts and which are suitable for direct feeding to the animal or for addition to the feed either directly or after an intermediate dilution or blending step. Typical carriers or diluents suitable for such compositions include, for example, distillers' dried grains, corn meal, citrus meal, fermentation residues, ground oyster shells, wheat shorts, molasses solubles, corn cob meal, edible bean mill feed, soya grits, crushed limestone and the like. The active hydrogenated avermectin compounds are intimately dispersed throughout the carrier by methods such as grinding, stirring, milling or tumbling. Compositions containing from about 0.005 to 2.0% by weight of the active compound are particularly suitable as feed premixes. Feed supplements, which are fed directly to the animal, contain from about 0.0002 to 0.3% by weight of the active compounds.

Such supplements are added to the animal feed in an amount to give the finished feed the concentration of active compound desired for the treatment and control of parastic diseases. Although the desired concentration of active compound will vary depending upon the factors previously mentioned as well as upon the particular avermectin derivative employed, the compounds of this invention are usually fed at concentrations of between 0.00001 to 0.002% in the feed in order to achieve the desired antiparasitic result.

The avermectin compounds of this invention are also useful in combatting agricultural pests that inflict damage upon crops while they are growing or while in storage. The compounds are applied using known techniques as sprays, dusts, emulsions and the like, to the growing or stored crops to effect protection from such agricultural pests.

In using the compounds of this invention, the individual substituted avermectin components may be prepared and used in that form. Alternatively, mixtures of two or more of the individual avermectin components may be used, as well as mixtures of the parent avermectin compounds, other avermectin compounds or other active compounds not related to avermectin, with the compounds of this invention.

In the isolation of the avermectin compounds, which serve as starting materials for the instant proceses, from the fermentation broth, the various avermectin compounds will be found to have been prepared in unequal amounts. In particular an "a" series compound will be prepared in a higher proportion than the corresponding "b" series compound. The difference between the "a" series and "b" series is constant throughout the avermectin compounds and consists of a sec-butyl group and an iso-propyl group respectively at the 25 position. This difference, of course, does not interfere with any of the instant reactions. In particular it may not be necessary to separate the "b" components from the related "a" component. Separation of these closely related compounds is generally not practiced since the "b" compound is present only in a small percent by weight, and the structural difference has negligible effect on the reaction processes and biological activities.

In particular it has been found that the starting materials for the compounds of this invention are very often prepared in a ratio of about 80% avermectin B1a or A1a and 20% avermectin B1b or A1b. Thus the preferred composition of this invention is one which contains about 80% of the "a" component and 20% of the "b" component.

The following examples are provided in order that this invention might be more fully understood; they are not to be construed as limitative of the invention.

The substituted avermectin derivatives prepared in the following examples are generally isolated as amorphous solids and not as crystalline solids. They are thus characterized analytically using techniques such as mass spectrometry, nuclear magnetic resonance, and the like. Being amorphous, the compounds are not characterized by sharp melting points, however, the chromatographic and analytical methods employed indicate that the compounds are pure.

In the following examples, the various starting materials therefor are avermectin compounds or derivatives of avermectin compounds. The avermectin compounds and the preparation and isolation thereof from fermentation broths are described in U.S. Pat. No. 4,310,519 issued Jan. 12, 1982. The selective 22,23-dihydro derivatives of avermectin compounds are described in U.S. Pat. No. 4,199,569 issued Apr. 22, 1980. The aglycone and monosaccharide derivatives of avermectin compounds are described in U.S. Pat. No. 4,206,205 issued Jan. 3, 1980.

EXAMPLE 1

Avermectin A1a/A1b 14,15 Epoxide

A solution of 5 mg (0.0056 mmoles) of avermectin A1a/A1b was dissolved in 0.1 ml of methylene chloride a separate solution of 46 mg of 85% metachloroperbenzoic acid in 10 ml of methylene chloride was prepared which solution affords 0.0227 mmoles per ml. 0.25 Ml of this metachloroperbenzoic acid solution was added to the avermectin A1a/A1b solution providing for 0.0057 mmole of metachloro per benzoic acid. The reaction mixture was stirred over night at room temperature and evaporated to dryness at 35° C. under a stream of nitrogen. The residue is placed on a preparative layer chromatography plates and multiply eluted with 2% methanol in chloroform affording a main band with an $R_f$ of 0.5 a smaller band with an $R_f$ of 0.4 and a very small band with an $R_f$ of 0.8. The very small band was discarded and mass spectroanalysis of the band with an $R_f$ of 0.4 indicated the presence of avermectin A1a/A1b-14,15-epoxide.

EXAMPLE 2

Avermectin B1a/B1b-8,9-Epoxide

A solution of 4.7 mg of 85% metachloroperbenzoic acid and 0.5 ml of fresh methylene chloride is prepared, is placed in a test tube, fitted with a septum and immersed in a dry ice acetone bath. There was added a solution of 0.5 ml of methylene chloride containing 20 mg of avermectin B1a/B1b. The reaction mixture is stirred under nitrogen at −70° C. for two hours and at −30° C. for 30 minutes. Then the reaction mixture was placed in an ice bath for 4 hr. and in a refrigerator for 2 days. The reaction mixture was placed on an 8×8 inch chromatography plate with a layer of 250 microns of silica gel and developed with 5% isopropanol in benzene three times. Two fractions are observed: the faster moving fraction weighing 6.4 mg; a slower moving fraction weighing 8.2 mg. The mass spectral and nuclear magnetic resonance analysis of both fractions indicate that the slow moving fraction was avermectin B1a/B1b-8,9-epoxide.

EXAMPLE 3

5-O-t-Butyldimethylsilyl 22,23-Dihydro Avermectin B1a/B1b-8,9-Epoxide

100 Mg of 22,23-dihydro 5-O-t-butyldimethylsylyl avermectin B1a/B1b is dissolved in 1.5 ml of methylene chloride and stirred in an ice bath under a stream of nitrogen. There was added dropwise 1.5 ml of methylene chloride solution containing 27 mg of 85% metachloroperbenzoic acid. The reaction mixture was stirred in an ice bath for 2½hr. at room temperature and allowed to stand in a refrigerator for 2 days. A solution of sodium bicarbonate was added and the mixture extracted three times with ether. The organic phases were combined and washed four times with water, dried over magnesium sulfate and evaporated to dryness under a stream of nitrogen to 100 mg of a white opaque glass. The glass was dissolved in methylene chloride and placed on two 1000 micron silica gel preparative layer chromatography plates and eluted three times with 20% ethyl acetate in methylene chloride. Four fractions were observed. The fastest moving fraction, (61.5 mg) was identified as 22,23-dihydro 5-O-t-butyldimethylsylyl avermectin B1a/B1b-8,9-epoxide. The third fastest (16 mg) was identified as 22,23-dihydro 5-O-t-butyldimethylsylyl avermectin B1a/B1b-14,15-epoxide. The slowest fraction (10 mg) was identified as 22,23-dihydro 5-O-t-butyldimethylsylyl avermectin B1a/B1b 8,9,14,15 bis-epoxide

EXAMPLE 4

22,23-Dihydro Avermectin B1a/B1b-8,9-Epoxide

In a flame dried test tube there was dissolved 100 mg of 22,23-dihydro avermectin B1a/B1b in 0.7 ml of dried methylene chloride. To the solution was added 1 mg of vanadyl acetyl acetonate followed by 19 microliters of 90% t-butylhydroperoxide. The reaction mixture was stirred for 24 hr. at room temperature. To the reaction mixture was added 2 ml of water, and the mixture was extracted three times with 3 ml of ether. The organic layers were combined and washed with water, dried over magnesium sulfate and evaporated to dryness under a stream of nitrogen affording 96 mg of an orange foam. Preparative layer chromatography on two plates of 1,000 micron layers of silica gel afforded a fraction of non-UV absorbing material weighing 45.5 mg as a clear glass. Nuclear magnetic resonance analysis of this material showed it to be 22,23-dihydro avermectin B1a/B1b-8,9-epoxide.

EXAMPLE 5

Avermectin-B2a/B2b-8,9-oxide.

A solution of 102 mg of avermectin-B2a/B2b in 1.0 ml of dry methylene chloride is stirred at room temperature in a 15 ml centrifuge tube. Appropiately 1 mg of vanadyl acetyl acetonate and 20 microliters of a 90% solution of t-butylhydroperoxide is added. After 24 hours stirring at room temperature, 2 ml of water is added to the reaction mixture and the crude product is isolated by repeated extractions with 3 ml portions of effluent. These effluent extracts are combined, washed with water and dried over magnesium sulfate. The ether layer is concentrated under a shear of nitrogen to about 100 mg of a yellow oil. This is further purified by preparative layer chromatography on silica gel plates eluting mehtylene chloride containing about 7% of methanol as eluent. The band leading UV absorption is extracted with an ethyl acetate-methanol solvent mixture concentrated in vacuo to a white foam and identified by $^1$H-NMR and mass spectra as avermectin-B2a/B2b-8,9-oxide. EXAMPLE 6

22,23-Dihydro Avermectin B1a/B1b monosaccharide-8,9-oxide

When 84 mg of 22,23 dihydro avermectin B1a/B1b monosaccharide are reacted according to the procedure of Example 5, the title compound is obtained.

What is claimed is:

1. A compound having the formula:

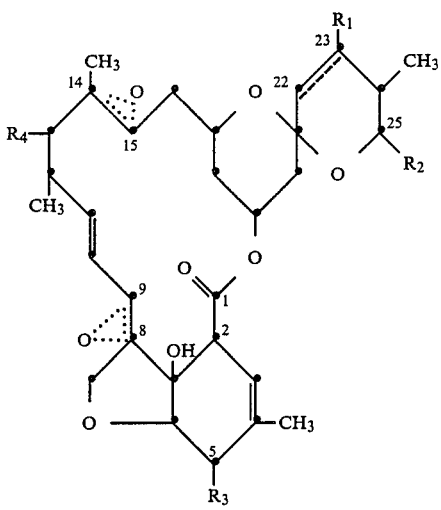

wherein the broken line at the 22,23-position indicates a single or a double bond; wherein R$_1$ is hydrogen or hydroxy provided that R$_1$ is present only when the broken line at the 22,23-position indicates a single bond;

R$_2$ is iso-propyl or sec-butyl;

R$_3$ is hydroxy or methoxy;

R$_4$ is hydroxy, α-L-oleandrosyloxy, or 4′-(α-L-oleandrosyl)-α-L-oleandrosyloxy; and the triangular figures at the 8,9 and 14,15 positions indicate that there is present a double bond or an epoxide, provided that at least one of the 8,9 and 14,15 positions is an epoxide.

2. The compound of claim 1 wherein the triangular figure at 8,9 is an epoxide and that at 14,15 is a double bond.

3. The compound of claim 2 which is selected from the group consisting of avermectin B1a and B1b-8,9-epoxide.

4. The compound of claim 2 which is selected from the group consisting of 22,23-dihydro avermectin B1a and B1b-8,9-epoxide.

5. The compound of claim 2 which is selected from the group consisting of avermectin B2a and B2b-8,9-epoxide.

6. The compound of claim 2 which is selected from the group consisting of avermectin B1a and B1b-8,9-epoxide α-L-oleandrosyloxy.

7. The compound of claim 2 which is selected from the group consisting of 22,23-dihydro avermectin B1a and B1b-8,9-epoxide α-L-oleandrosyloxy.

8. The compound of claim 1 wherein the triangular figure at 8,9 is a double bond and that at 14,15 is an epoxide.

9. The compound of claim 8 which is selected from the group consisting of avermectin A1a and A1b-14,15-epoxide.

10. The compound of claim 8 which is selected from the group consisting of avermectin in B1a and B1b-14,15-epoxide.

11. The compound of claim 8 which is selected from the group consisting of 22,23-dihydro avermectin B1a and B1b-14,15-epoxide.

12. The compound of claim 1 wherein both triangular figures represent epoxides.

13. The compound of claim 12 which is selected from the group consisting of avermectin B1a and/or B1b 8,9,14,15-bis epoxide.

14. The compound of claim 12 which is selected from the group consisting of 22,23-dihydro avermectin B1a and B1b-8,9,14,15-bis epoxide.

15. A method for the treatment of parasitic infections which comprises administering to an animal infected with parasites an effective amount of a compound of claim 1.

16. A composition useful for treating animals infected with parasites which comprises an inert carrier and a compound of claim 1.

* * * * *